United States Patent [19]
Knowlton

[11] Patent Number: 5,981,781
[45] Date of Patent: Nov. 9, 1999

[54] SOYBEAN OIL HAVING HIGH OXIDATIVE STABILITY

[75] Inventor: Susan Knowlton, Elkton, Md.

[73] Assignee: E. I. du Pont de Nemours and Company, Wilmington, Del.

[21] Appl. No.: 09/106,877

[22] Filed: Jun. 30, 1998

Related U.S. Application Data

[63] Continuation of application No. PCT/US97/07028, Apr. 25, 1997
[60] Provisional application No. 60/016,154, Apr. 26, 1996.
[51] Int. Cl.$^6$ .............................. C07C 53/00; A23D 7/00
[52] U.S. Cl. ......................... 554/224; 554/223; 426/607; 426/601
[58] Field of Search .................................. 426/607, 601; 554/223, 224

[56] References Cited

U.S. PATENT DOCUMENTS

| | | | |
|---|---|---|---|
| 5,399,275 | 3/1995 | Lange et al. | 252/49.008 |
| 5,534,425 | 7/1996 | Fehr et al. | 435/172.1 |

FOREIGN PATENT DOCUMENTS

| | | | |
|---|---|---|---|
| 93/17566 | 9/1993 | WIPO | A23D 9/00 |
| 94/11516 | 5/1994 | WIPO | C12N 15/53 |
| 96/06936 | 3/1996 | WIPO | C12N 15/55 |

OTHER PUBLICATIONS

Neff, W.E. et al., Oxidative Stability of Purified Canola Oil Triacylglycerols with Altered Fatty Acid Compositions as Affected by Triacylglycerol Composition and Structure, JAOCS, 71, No. 10, 1101–1109, Oct. 1994.

Smouse, Thomas H., Factors Affecting Oil Quality and Stability, *Methods to Assess Quality and Stability of Oils and Fat–Containing Foods*, Chapter 2, 17–18, ed. K. Warner and N.A.M. Eskin, AOCS Press, 1995.

Warner, K. et al., Effect of fatty acid composition of oils on flavor and stability of fried foods, *J. Am. Oil Chem. Soc.*, 74(4), 347–356 (abstract), 1997.

Journal of American Oil Chemists, oxidation stability of blends and interesterified blend of soybean oil and palm olein, 1994, vol. 71, No. 10, Neff et al.

S. K. B. Ellis et al., Performance of High Oleic Soybean Oil: An Alternative to Hydrogenated Fats, *Cereal Foods World*, 41, No.7, Abstract 123, 569, 1996.

B. F. Carver et al., Developmental Changes in Acyl–Composition of Soybean Seed Selected for High Oleic Acid Concentration, *Crop Science*, 24, No. 6, 1016–1019, 1984.

W. E. Neff et al., Photooxidation of Soybean Oils as Affected by Triacylglycerol Composition and Structure, *Journal of the American Oil Chemists' Society*, 70, No. 2, 163–168, Feb., 1993.

Y. Takagi et al., Inheritance of high oleic acid content in the seed oil of soybean mutant M23, *Theor. Appl. Genet.*, 92, 179–182, 1996.

S. M. Rahman et al., High Oleic Acid Mutant in Soybean Induced by X–Ray Irradiation, *Biosci. Biotech. Biochem.*, 58, No. 6, 1070–1072, 1994.

L. A. T. Honary, An Investigation of the Use of Soybean Oil in Hydraulic Systems, *Bioresource Technology*, 56, 41–47, 1996.

*Primary Examiner*—Paul J. Killos
*Assistant Examiner*—J. Parsa

[57] ABSTRACT

A high oleic soybean oil having high oxidative stability is disclosed. This oil has an AOM induction time of greater than 50 hours. Oxidative stability is achieved without the need for hydrogenation or the addition of an antioxidant.

8 Claims, 3 Drawing Sheets

SOYBEAN OIL HAVING HIGH OXIDATIVE STABILITY

This application is provisional application of 60/016,154 filed on Apr. 26, 1996. This is also a continuation of a PCT application Ser. No. PCT/US97/07028 filed on Apr. 25, 1997.

FIELD OF THE INVENTION

This invention relates to soybean oil and, in particular, to high oleic soybean oil that does not require hydrogenation or the addition of antioxidants to achieve high oxidative stability.

BACKGROUND OF THE INVENTION

Soybean oil is currently the predominant plant oil in the world. However, soybean oil is relatively unstable to oxidation and therefore its use is limited to applications in which a high degree of oxidative stability is not required. Soybean oil contains high levels of polyunsaturated fatty acids and is more prone to oxidation than oils with higher levels of monounsaturated and saturated fatty acids. The higher the degree of unsaturation in an oil the more likely that the oil will go rancid (oxidize). Oxidation leads to the development of off flavors and odors in the oil as a result of the degradation process. Oils with high levels of polyunsaturated fatty acids are not often used in applications that require a high degree of oxidative stability, such as cooking for a long period of time at an elevated temperature.

Several methods are available to increase the stability of soybean oil. One commonly used method is catalytic hydrogenation, a process that reduces the number of double bonds and raises the melting point of the fat. Consequently, hydrogenation also increases the saturated fatty acid content of oil. Another approach to increase oxidative stability is through the addition of antioxidants.

Each of these approaches suffers from one or more drawbacks, for example, hydrogenation of oils has been linked to health, environmental and food quality concerns. One known consequence of hydrogenation of oils is the production of trans fatty acid isomers which have been associated with deleterious health effects including increased risk of coronary heart disease. (Food Product Design, November 1994). In the case of antioxidants, some are very expensive to acquire and not all antioxidants withstand high temperatures. In addition, in many cases a food manufacturer does not want to use oils with added antioxidants if a label with unadulterated ingredients is desired. Thus, an oil which has a high oxidative stability under high temperatures without requiring the addition of antioxidants is very desirable.

U.S. Pat. No. 5,260,077, issued to Carrick et al. on Nov. 9, 1993, discloses a method of stabilizing triglyceride oils of high oleic acid content by addition of tocopherol, a natural antioxidant. The combination of the high oleic oil and tocopherol results in a stable composition suitable for deep frying.

World Patent Publication W094/11516, published on May 26, 1994, discloses the isolation and characterization of nucleic acid fragments encoding fatty acid desaturase enzymes, and their use to produce oil seeds with altered levels of unsaturated fatty acids.

World Patent Publication WO90/10380, published on Sep. 20, 1990, discloses a homogeneous assemblage of mature rapeseeds having an oleic acid content of at least 79 weight percent with respect to total fatty acids and an erucic acid content of not more than 2 weight percent. These seeds are alleged to yield a vegetable oil having high heat stability; this vegetable oil may be used as a frying oil.

European Patent Publication EP 323,753, published on Jul. 12, 1989, discloses mature rapeseeds having, by weight, a total fatty acid content a high oleic acid content of at least 79% and not more than 2% erucic acid. The oil derived from these seeds is said to have increased heat stability.

"Clear Valley® Canola Oil" Technical Bulletin No. SA 2069 (1995 Cargill Foods) discloses a natural canola salad oil with low levels of linolenic acid and an oxidative stability of at least 25 AOM hours.

"Van Den Bergh Design NH" Technical Bulletin No. FI93184 discloses a natural canola oil with a high level of oleic acid and an oxidative stability of at least 20 AOM hours.

"SVO Trisun 80" Technical Data Sheet discloses a natural sunflower oil with 80% oleic acid and an oxidative stability of at least 35 AOM hours. "SVO Trisun Extra" Technical Data Sheet discloses a natural sunflower oil with 85% oleic acid and an oxidative stability of at least 60 AOM hours. "SVO HS-Natural" Technical Data Sheet discloses a high oleic (80%) sunflower oil with added natural tocopherols (0.2%) and an oxidative stability of at least 60–70 AOM hours.

"Kraft Food Ingredients Soy•LL" Technical Data Sheet discloses a low linolenic soybean oil with an oxidative stability of 23–25 hours.

Warner, K. et al. ((1989) JAOCS 66(4): 558–564) disclose the flavor and oxidative stability of soybean, sunflower, and low erucic acid rapeseed oils. The oxidative stability of non-hydrogenated soybean oil, held at 100° C. for 1, 2, or 3 days, is reported as 13.5, 15.0, 14.0 AOM hours, respectively. White, P. J. and Miller, L. A. ((1989) JAOCS 65(8): 1334–1338) disclose the oxidative stabilities of low linolenic acid, high stearic acid, and common soybean oils. Mounts, T. L et al. ((1989) JAOCS 65(4): 624–628) disclose the effect of altered fatty acid composition on soybean oil stability.

U.S. Pat. No. 4,627,192 discloses a sunflower seed having an oleic acid content of 80% or greater. U.S. Pat. No. 4,743,402 discloses a high oleic sunflower oil.

FR 2617675, published on Jan. 13, 1989, discloses groundnut seeds with an oleic acid content of 74–84% and linoleic acid content about 2–8%. The low linoleic acid content is reported to ensure high storage stability.

World Patent Publication WO91/11906, published on Aug. 22, 1991, discloses safflower seeds having an oleic or linoleic acid content of at least 80%.

Oxidative stability is also an important characteristic for industrial oil applications. This problem is particularly acute for triglyceride oils which tend to deteriorate easily due to their high degree of unsaturation. The oxidation proceeds via a mechanism which is initiated by the formation of a free radical and occurs rather easily in triglyceride oils due to the high content of active methylene groups adjacent to the double bonds. The overall effect is a high susceptibility of the oil to oxidation, which is further complicated by contact of the oil with metals, such as iron and copper, present in the equipment or material to be lubricated. Metals act as catalysts in the oxidation process and accelerate degradation of the oil.

U.S. Pat. No. 5,580,482, issued to Chasan et al. on Dec. 3, 1996, discloses lubricant compositions stabilized against the effects of heat and oxygen.

U.S. Pat. No. 5,413,725, issued to Lal et al. on May 9, 1995, discloses pour point depressants for monounsaturated vegetable oils and for high monounsaturated vegetable oils/biodegradable base and fluid mixtures.

U.S. Pat. No. 5,399,275, issued to Lange et al. on Mar. 21, 1995, discloses environmentally friendly viscosity index improving compositions.

SUMMARY OF THE INVENTION

The present invention is directed to a high oleic soybean oil having high oxidative stability which comprises a C18:1 content of greater than 65% of the fatty acid moieties in the oil, a combined C18:2 and C18:3 content of less than 20% of the fatty acid moieties in the oil and an active oxygen method induction time of greater than 50 hours wherein said oxidative stability is achieved without the addition of an antioxidant. The oil of this invention can be used as a blending source to make a blended oil product. It can be used in the preparation of food.

DETAILED DESCRIPTION OF THE INVENTION

The present invention relates to a high oleic soybean oil having high oxidative stability which comprises a C18:1 fatty acid content of greater than 65% by weight, combined levels of C18:2 and C18:3 fatty acid content of less than 20% by weight, and an active oxygen method of greater than 50 hours wherein said oxidative stability is achieved without the addition of an antioxidant. A soybean oil with "high oxidative stability" is a soybean oil that is less susceptible to oxidative degradation when compared to normal soybean oil.

A high oleic soybean seed is a soybean seed wherein oleic acid accounts for greater than 65 percent of the fatty acid moieties in the oil and, preferably, greater than 75 percent of the fatty acid moieties in the oil. Preferred high oleic soybean oil starting materials are disclosed in World Patent Publication WO94/11516, the disclosure of which is hereby incorporated by reference. The soybeans used in the present invention are described in Example 1 below.

The high oleic soybean oil of this invention has a C18:1 content of 65 to 85% of the fatty acid moieties, a combined C18:2 and C18:3 content of less than 20% of the fatty acid moieties. Preferably, the oil of the invention has a C18:1 content of greater than about 70% of the fatty acid moieties, a combined C18:2 and C18:3 content of less than 15% of the fatty acid. More preferably, the oil of the invention has a C18:1 content of greater than about 75% of the fatty acid moieties, a combined C18:2 and C18:3 content of less than 10% of the fatty acid moieties. Most preferably, the oil of the invention has a C18:1 content of greater than about 80% of the fatty acid moieties, a combined C18:2 and C18:3 content of less than 10% of the fatty acid.

A particularly advantageous feature of the present invention is that there is no need for hydrogenation or other fractionation of the oil to achieve high oxidative stability. Moreover, it is not necessary to add antioxidants, such as natural antioxidants like tocopherols, to the compositions of the invention in order to increase their stability.

A number of methods are well known to those skilled in the art for determining oxidative stability. The most commonly used method is the Active Oxygen Method (AOM). This is an accelerated oxidation test in which an oil is aerated under a constant, elevated temperature (97.8° C.) and degradation is monitored by measuring peroxide accumulation. The end point, or induction time, is determined by the number of hours required to reach a peroxide value of 100 meq/kg. Thus, the longer the induction time the more stable the oil. Almost all commercial oil samples specify an AOM induction time as a component of the technical data sheet.

The AOM induction time for the high oleic soybean oil of the invention is greater than 50 hours. Preferably, the AOM induction is greater than 75 hours and, most preferably, greater than 100 hours or even greater than 140 hours.

Another standard method now commonly used to evaluate the stability of commercial cooking oils is the Oxidative Stability Index (OSI) which is measured automatically using a machine manufactured by Ominion, Inc. of Rockland, Mass., USA.

The OSI machine works by bubbling air through oil heated to 110° C. As the oil oxidizes, volatile organic acids, primarily formic acid, is formed which can be collected in distilled water in a cell. The machine constantly measures the conductivity of the distilled water and the induction period is determined as the time it takes for this conductivity to begin a rapid rise. Although the data derived from the two methods do not always have a straight correlation, the OSI induction time values for most oils are generally about half those of the AOM derived values.

The OSI induction time value for the high oleic soybean oil of the invention is greater than 25 hours. Preferably, the OSI induction time value is greater than 50 hours and, most preferably, greater than 75 hours.

Vegetable oils are often used in high temperature applications. Oil oxidation is accelerated in the presence of heat. It is important that an oil be able to withstand these conditions for applications such as frying, baking, roasting, etc. In some cases, antioxidants may be added to improve stability but not all antioxidants withstand high temperatures. In addition, in many cases a food manufacturer does not want to use oils with added antioxidants if a label with unadulterated ingredients is desired. Therefore, an oil which is stable to oxidation under high temperatures in the absence of any additives or other processing is highly desirable. Overheating of oils often leads to thermal polymerization of the oil and oxidation products resulting in a gummy, varnish-like buildup on the equipment used for heating and excessive foaming of the oil. As a result of oxidation, a variety of degradation products are formed depending on the conditions under which the oil is exposed. High temperature stability can be evaluated by exposing the oils to high temperature and monitoring the formation of the undesirable degradation products. These include both volatile and nonvolatile products and may be hydrocarbons, alcohols, aldehydes, ketones, and acids. The nonvolatile components can be further classified into polar and polymerized compounds. The polar and polymerized compounds present in a degraded oil can be analyzed directly by reverse phase high performance liquid chromatography as described in Lin, S. S., 1991, Fats and oils oxidation. Introduction to Fats and Oils Technology (Wan, P. J. ed.), pages 211–232, Am. Oil Chem. Soc.

The oil of this invention can be used in a variety of applications. In general, oxidative stability is related to flavor stability. The oil of this invention can be used in the preparation of foods. Examples include, but are not limited to, uses as ingredients, as coatings, as salad oils, as spraying oils, as roasting oils, and as frying oils. Foods in which the oil may be used include, but are not limited to, crackers and snack foods, confectionery products, syrups and toppings, sauces and gravies, soups, batter and breading mixes, baking mixes and doughs. Foods which incorporate the oil of this invention may retain better flavor over longer periods of time due to the improved stability against oxidation imparted by this oil.

The oils of this invention can also be used as a blending source to make a blended oil product. By a blending source, it is meant that the oil of this invention can be mixed with other vegetable oils to improve the characteristics, such as fatty acid composition, flavor, and oxidative stability, of the other oils. The amount of oil of this invention which can be used will depend upon the desired properties sought to be achieved in the resulting final blended oil product. Examples of blended oil products include, but are not limited to, margarines, shortenings, frying oils, salad oils, etc.

In another aspect, the oils of this invention can be subjected to further processing such as hydrogenation, fractionation, interesterification or fat splitting (hydrolysis).

In still another aspect, this invention concerns by-products made during the production of the oils of this invention.

Methods for the extraction and processing of soybean seeds to produce soybean oil and meal are well known throughout the soybean processing industry. In general, soybean oil is produced using a series of steps which accomplish the extraction and purification of an edible oil product from the oil bearing seed. Soybean oils and soybean byproducts are produced using the generalized steps shown in the diagram below.

Soybean seeds are cleaned, tempered, dehulled, and flaked which increases the efficiency of oil extraction. Oil extraction is usually accomplished by solvent (hexane) extraction but can also be achieved by a combination of physical pressure and/or solvent extraction. The resulting oil is called crude oil. The crude oil may be degummed by hydrating phospholipids and other polar and neutral lipid complexes which facilitate their separation from the nonhydrating, triglyceride fraction (soybean oil). The resulting lecithin gums may be further processed to make commercially important lecithin products used in a variety of food and industrial products as emulsification and release (antisticking) agents. Degummed oil may be further refined for the removal of impurities; primarily free fatty acids, pigments, and residual gums. Refining is accomplished by the addition of caustic which reacts with free fatty acid to form soap and hydrates phosphatides and proteins in the crude oil. Water is used to wash out traces of soap formed during refining. The soapstock byproduct may be used directly in animal feeds or acidulated to recover the free fatty acids. Color is removed through adsorption with a bleaching earth which removes most of the chlorophyll and carotenoid compounds. The refined oil can be hydrogenated resulting in fats with various melting properties and textures. Winterization (fractionation) may be used to remove stearine from the hydrogenated oil through crystallization under carefully controlled cooling conditions. Deodorization which is principally steam distillation under vacuum, is the last step and is designed to remove compounds which impart odor or flavor to the oil. Other valuable byproducts such as tocopherols and sterols may be removed during the deodorization process. Deodorized distillate containing these byproducts may be sold for production of natural vitamin E and other high value pharmaceutical products. Refined, bleached, (hydrogenated, fractionated) and deodorized oils and fats may be packaged and sold directly or further processed into more specialized products. A more detailed reference to soybean seed processing, soybean oil production and byproduct utilization can be found in Erickson, 1995, Practical Handbook of Soybean Processing and Utilization, The American Oil Chemists' Society and United Soybean Board.

Hydrogenation is a chemical reaction in which hydrogen is added to the unsaturated fatty acid double bonds with the aid of a catalyst such as nickel. High oleic soybean oil contains unsaturated oleic, linoleic, and linolenic fatty acids and each of these can be hydrogenated. Hydrogenation has two primary effects. First, the oxidative stability of the oil is increased as a result of the reduction of the unsaturated fatty acid content. Second, the physical properties of the oil are changed because the fatty acid modifications increase the melting point resulting in a semi-liquid or solid fat at room temperature.

There are many variables which affect the hydrogenation reaction which in turn alter the composition of the final product. Operating conditions including pressure, temperature, catalyst type and concentration, agitation and reactor design are among the more important parameters which can be controlled. Selective hydrogenation conditions can be used to hydrogenate the more unsaturated fatty acids in preference to the less unsaturated ones. Very light or brush hydrogenation is often employed to increase stability of liquid oils. Further hydrogenation converts a liquid oil to a physically solid fat. The degree of hydrogenation depends on the desired performance and melting characteristics designed for the particular end product. Liquid shortenings, used in the manufacture of baking products, solid fats and shortenings used for commercial frying and roasting operations, and base stocks for margarine manufacture are among the myriad of possible oil and fat products achieved through hydrogenation. A more detailed description of hydrogenation and hydrogenated products can be found in Patterson, H. B. W., 1994, Hydrogenation of Fats and Oils: Theory and Practice. The American Oil Chemists' Society.

Interesterification refers to the exchange of the fatty acyl moiety between an ester and an acid (acidolysis), an ester and an alcohol (alcoholysis) or an ester and ester (transesterification). Interesterification reactions are achieved using chemical or enzymatic processes. Random or directed transesterification processes rearrange the fatty acids on the triglyceride molecule without changing the fatty acid composition. The modified triglyceride structure may result in a fat with altered physical properties. Directed interesterfication reactions using lipases are becoming of increasing interest for high value specialty products like cocoa butter substitutes. Products being commercially produced using interesterification reactions include but are not limited to shortenings, margarines, cocoa butter substitutes and structured lipids containing medium chain fatty acids and polyunsaturated fatty acids. Interesterification is further discussed in Hui, Y. H., 1996, Bailey's Industrial Oil and Fat Products, Volume 4, John Wiley & Sons.

Fatty acids and fatty acid methyl esters are two of the more important oleochemicals derived from vegetables oils. Fatty acids are used for the production of many products such as soaps, medium chain triglycerides, polyol esters, alkanolamides, etc. Vegetable oils can be hydrolyzed or split into their corresponding fatty acids and glycerine. Fatty acids produced from various fat splitting processes may be used crude or more often are purified into fractions or individual fatty acids by distillation and fractionation. Purified fatty acids and fractions thereof are converted into a wide variety of oleochemicals, such as dimer and trimer acids, diacids, alcohols, amines, amides, and esters. Fatty acid methyl esters are increasingly replacing fatty acids as starting materials for many oleochemicals such as fatty alcohols, alkanolamides, a-sulfonated methyl esters, diesel oil components, etc. Glycerine is also obtained by the cleavage of triglycerides using splitting or hydrolysis of vegetable oils. Further references on the commercial use of fatty acids and oleochemicals may be found in Erickson, D. R., 1995, Practical Handbook of Soybean Processing and Utilization, The American Oil Chemists' Society, and United Soybean Board; Pryde, E. H., 1979, Fatty Acids, The American Oil Chemists' Society; and Hui, Y. H., 1996, Bailey's Industrial Oil and Fat Products, Volume 4, John Wiley & Sons.

In another aspect, this invention concerns the industrial use of the soybean oil of this invention for industrial applications such as an industrial lubricant for a variety of end uses, as a hydraulic fluid, etc. The industrial use of vegetable oils as a base fluid for lubricants has been known for many years. However, interest has intensified due to environmental concerns over the use of petroleum oils in environmentally sensitive areas. Vegetable oils are readily biodegradable, have low toxicity and have good lubricant characteristics. However, high pour points and rapid oxidation at high temperatures limit their use. Since the soybean oil of this invention is low in polyunsaturates, as discussed herein, and has high oxidative stability and high temperature stability, these characteristics also make the soybean oil of this invention desirable for industrial applications such as an industrial fluid, i.e., as industrial lubricant or as a hydraulic fluid, etc. Additives which can be used to make industrial lubricants and hydraulic fluids are commercially available. Indeed, some additives have been specially formulated for use with high oleic vegetable oils. Additives generally contain antioxidants and materials which retard foaming, wear, rust, etc.

One common method for measuring oxidative stability of industrial fluids is the rotary bomb oxidation test (ASTM D-2272). The performance of the oil of this invention when compared to commercially available products using the rotary bomb oxidation test is set forth in the example below.

EXAMPLES

The present invention is further defined in the following Examples, in which all parts are by weight, percentages are by weight (to volume), and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1

High Oleic Soybeans

The production of a soybean oil high in oleic acid and low in polyunsaturated fatty acids, without the need to perform chemical processing of the oil, requires the availability of soybeans which have a high content of oleic acid in the fatty acid fraction. High oleic soybeans were prepared by recombinant manipulation of the activity of oleoyl 12-desaturase. In soy (*Glycine max*) there are two genes for this activity, one of which (GmFad 2-1) is expressed only in the developing seed (Heppard et al. (1996) Plant Physiol. 110:311–319). The expression of this gene increases during the period of oil deposition, starting around 19 days after flowering, and its gene product is responsible for the synthesis of the polyunsaturated fatty acids found in soybean oil. GmFad 2-1 is described in detail by Okuley, J. et al. (1994) Plant Cell 6:147–158 and in W094/11516. It is available from the ATCC in the form of plasmid pSF2-169K (ATCC accession number 69092). The other gene (GmFad 2-2) is expressed in the seed, leaf, root and stem of the soy plant at a constant level and is the "housekeeping" 12-desaturase gene. The Fad 2-2 gene product is responsible for the synthesis of polyunsaturated fatty acids for cell membranes.

GmFad 2-1 was placed under the control of a strong, seed-specific promoter derived from the α'-subunit of the soybean (*Glycine max*) β-conglycinin gene. This promoter allows high level, seed specific expression of the trait gene. It spans the 606 bp upstream of the start codon of the α' subunit of the Glycine max β-congylcinin storage protein. The β-conglycinin promoter sequence represents an allele of the published β-conglycinin gene (Doyle et al., (1986) J. Biol. Chem. 261:9228–9238) having differences at 27 nucleotide positions. It has been shown to maintain seed specific expression patterns in transgenic plants (Barker et al., (1988) Proc. Natl. Acad. Sci. 85:458–462 and Beachy et al., (1985) EMBO J. 4:3047–3053). The reading frame was terminated with a 3' fragment from the phaseolin gene of green bean (*Phaseolus vulgaris*). This is a 1174 bp stretch of sequences 3' of the *Phaseolus vulgaris* phaseolin gene stop codon (originated from clone described in Doyle et al., 1986).

The GmFad 2-1 open reading frame (ORF) was in a sense orientation with respect to the promoter so as to produce a gene silencing of the sense GmFad 2-1 cDNA and the endogenous GmFad 2-1 gene. This phenomenon, known as "sense suppression" is an effective method for deliberately turning off genes in plants and is described in U.S. Pat. No. 5,034,323.

For maintenance and replication of the plasmid in *E. coli* the GmFad 2-1 transcriptional unit described above was cloned into plasmid pGEM-9z(-) (Promega Biotech, Madison Wis., USA).

For identification of transformed soybean plants the β-glucuronidase gene (GUS) from *E. coli* was used. The cassette used consisted of the three modules; the Cauliflower Mosaic Virus 35S promoter, the β-glucuronidase gene (GUS) from *E. coli* and a 0.77 kb DNA fragment containing the gene terminator from the nopaline synthase (NOS) gene of the Ti-plasmid of *Agrobacterium tumefaciens*. The 35S promoter is a 1.4 kb promoter region from CaMV for constitutive gene expression in most plant tissues (Odell et al. (1985) Nature 303:810–812), the GUS gene a 1.85 kb fragment encoding the enzyme β-glucuronidase (Jefferson et al. (1986) PNAS USA 83:8447–8451) and the NOS terminator a portion of the 3' end of the nopaline synthase coding region (Fraley et al., (1983) PNAS US 80:48034807). The GUS cassette was cloned into the GmFad 2-1/pGEM-9z(-) construct and was designated pBS43.

Plasmid pBS43 was transformed into meristems of the elite soybean line A2396, by the method of particle bombardment (Christou et al., (1990) Trends Biotechnol. 8:145–151). Fertile plants were regenerated using methods well known in the art.

From the initial population of transformed plants, a plant was selected which was expressing GUS activity and which was also positive for the GmFad 2-1 gene (Event 260-05) when evaluated by PCR. Small chips were taken from a number of R1 seeds of plant 260-05 and screened for fatty acid composition. The chipped seed was then planted and germinated. Genomic DNA was extracted from the leaves of the resulting plants and cut with the restriction enzyme Bam HI. The blots were probed with a phaseolin probe.

From the DNA hybridization pattern it was clear that in the original transformation event the GmFad 2-1 construct had become integrated at two different loci in the soybean genome. At one locus (Locus A) the GmFad 2-1 construct was causing a silencing of the endogenous GmFad 2-1 gene, resulting in a relative oleic acid content of about 85% (compared with about 20% in elite soybean varieties). At locus A there were two copies of pBS43. On the DNA hybridization blot this was seen as two cosegregating bands. At the other integration locus (Locus B) the GmFad 2-1 was over-expressing, thus decreasing the oleic acid content to about 4%.

Fourth generation segregant lines (R4 plants), generated from the original transformant, were allowed to grow to maturity. R4 seeds, which contained only the silencing Locus A (e.g., G94-1) did not contain any detectable GmFad 2-1 mRNA (when measured by Northern blotting) in samples recovered 20 days after flowering. GmFad 2-2 mRNA, although reduced somewhat compared with controls, was not suppressed. Thus the GmFad 2-1 sense construct had the desired effect of preventing the expression of the GmFad 2-1 gene and thus increasing the oleic acid content of the seed. All plants homozygous for the GmFad 2-1 silencing locus had an identical Southern blot profile over a number of generations. This indicates that the insert was stable and at the same position in the genome over at least four generations. A summary of the oleic acid contents found in the different generations of recombinant soybean plants and seeds is presented in Table 1.

TABLE 1

| Plant ID | Generation Planted[a] | Seed Analyzed[a] | Bulk Oleic Acid (%) |
| --- | --- | --- | --- |
| G253 | R0:1 | R1:2 | 84.1% |
| G276 | R0:1 | R1:2 | 84.2% |
| G296 | R0:1 | R1:2 | 84.1% |
| G313 | R0:1 | R1:2 | 83.8% |
| G328 | R0:1 | R1:2 | 84.0% |
| G168-187 | R1:2 | R2:3 | 84.4% |
| G168-171 | R1:2 | R2:3 | 85.2% |
| G168-59-4 | R2:3 | R3:4 | 84.0% |
| G168-72-1 | R2:3 | R3:4 | 84.1% |
| G168-72-2 | R2:3 | R3:4 | 84.5% |
| G168-72-3 | R2:3 | R3:4 | 84.3% |
| G168-72-4 | R2:3 | R3:4 | 83.3% |

[a]R0:1 indicates the seed and the plant grown from seed after selfing of the first generation transformant. R1:2 indicates the seed and the plant grown from seed after selfing of the second generation transformant. R2:3 indicates the seed and the plant grown from seed after selfing of the third generation transformant. R3:4 indicates the seed and the plant grown from seed after selfing of the fourth generation transformant.

Example 2

High Oleic Soybean Oil Extraction and Processing

High oleic and normal soybean oils each were produced on the laboratory bench or at a commercial pilot plant using industry standard methods as described below. Commercial samples of other high stability oils and shortenings used for comparison were obtained from the manufacturers and stored frozen under nitrogen. These included samples of soybean frying oil, clear liquid shortening, heavy duty shortening, low linolenic soybean oil, and high oleic canola oil. High oleic corn oil was produced using industry standard conditions similar to those described above.

Part A: Large (pilot plant) scale processing of oil

Harvested soybeans (97.5 kg) were tempered by spraying the seed with water to raise the moisture to 8.7%. The water and seed were blended for approximately 10 minutes and allowed to equilibrate for approximately 21 hours. Tempered seed was cracked using a Ferrell-Ross Cracking Roll set at 3.5 on the cracking roll scale. Hulls were separated on a Kice Multi-aspirator Model 6F6 using a differential air pressure of 0.8–1.2 inches of water. The aspirated soybean meats were cooked in a two tray Simon-Rosedowns cooker heated to approximately 40° C. for 10–30 minutes. Warmed soybean meats were dropped into the second tray and heated to 60–75° C. for 15–25 minutes. The cooked soybean meats were flaked to a thickness of approximately 0.4 mm in a E. R. and F. Turner Flaking Roll. The resulting soybean flakes were extracted with hexane in a Crown Iron Works Loop Extractor (Type II) using a total residence time of 60 minutes and a solvent-to-solids ratio of approximately 1.5:1 (wt:wt). The solvent temperature was 50–60° C. The miscella (hexane/oil mixture) was desolventized using a Tetra-Laval Scraped Surface Heat Exchanger followed by complete desolventization in the lab using a rotary evaporator. The crude oil was collected and held under nitrogen until further processing.

Crude oil was water degummed in the following manner. The oil was heated to 60–70° C. and a volume of 90° C. water equivalent to 2% of the oil volume was added and mixed for 15 minutes at 75–80° C.; solids were then separated by centrifugation. Degummed oil was refined by heating to 70–80° C. A volume of an 85% phosphoric acid solution equivalent to 0.1% of the degummed oil volume was added and the solution mixed for 30 minutes. Enough NaOH was added to reach 16 Bé to neutralize free fatty acids; an additional 0.08% w/w excess of NaOH was added and the solution mixed for 30 minutes while heating to 80–85° C. Solids were separated by centrifugation. The oil was water-washed by heating to 75–80° C. and adding 95° C. water to 10% (v/v), mixed for 10 minutes at 80–90° C., and centrifuged. Water-washed oil was bleached by loading 1200 g of oil into a 2L Parr reactor and adding a bleaching clay (Clarion 470 SA; American Colloid Co.) to 0.5% (w/w) under vacuum and heating to 110° C. for 30 minutes before cooling to 65° C. The oil was removed and 30 g "filter aid" was added and the oil filtered. These steps were repeated until all the oil was bleached. The oil was deodorized by loading 2200 g into 5 L glass deodorizer under vacuum and heated to 100° C. Steam was added at 3%(w/w)/h and the oil was brought to 240° C. with continuous sparging for 1 h at temperature. The oil was then cooled to 70° C. with sparging and the oil removed from the deodorizer. Thirty ppm citric acid was added to mimic industry standards during deodorization. Deodorized oil was stored frozen under nitrogen.

Part B: Small (laboratory) scale processing of oil

Harvested soybeans were heated in the microwave to 180° F., cooled to room temperature and cracked using a Roskamp TRC 650-6 Crack and Roll. Soybean hulls were removed using a Kice Aspirator and the remaining meats were heated to 180° F. and flaked in a Roskamp TRC 912 Flake and Roll. Crude oil was extracted in a glass, water-jacketed extraction vessel heated to 60° C. for 45 minutes using a solvent to solids ratio of approximately 4:1. The hexane/oil miscella was collected and the extraction repeated. The miscella was desolventized using a rotary evaporator leaving crude oil.

A volume of an 85% phosphoric acid solution equal to 0.1% (v/v) of the crude oil was added and the solution heated to 65–70° C. for 10 minutes while stirring. Warm (60° C.) NaOH (8% aqueous solution) was added dropwise to the oil to neutralize the free fatty acids and the $H_3PO_4$ with an additional 0.2% wt/wt excess. The solution was stirred for five minutes and the solids separated by centrifugation. The oil was water washed by adding hot water to 20% (v/v) as the sample was heated to 90° C. with rapid agitation. The oil and water were allowed to cool at room temperature for 10 minutes and then separated by centrifugation. The oil was dehydrated using very rapid agitation under vacuum at 85–95° C. for 30 minutes or until all moisture (bubbles, condensation) had been removed. The vacuum was then broken with nitrogen. The oil was bleached by adding 2% (wt/wt) Activated Bleaching Earth (AOCS #Z1077) and the solution mixed under vacuum for 30 minutes at 85–95° C. before cooling to 80° C. The vacuum was broken with nitrogen and 1% (wt/wt) of diatomaceous earth was added and the mixture filtered through a prepared bed of diatomaceous earth.

Citric acid was added to approximately 50 ppm, and the oil was deodorized at 240° C. with steam (4 mL water per 100 g oil) in a glass deodorizer for approximately 1 hour. The oil was cooled to 80° C. with sparging, and it was further cooled to 40° C. under nitrogen. The refined, bleached, and deodorized oil was stored frozen under a nitrogen atmosphere.

Example 3

Compositional Analysis

Oils produced in Example 2 were analyzed for composition as described below. Compositional data for the oils is given in Table 2.

Fatty acid composition: Fatty acid composition was determined essentially by the methods described in AOCS Ce 1c-89. Fatty acid methyl esters were prepared as follows. Ten µL oil was mixed with 1 mL hexane and 0.25 mL of a 3% sodium methoxide solution for 30 minutes. Acetic acid (0.1 mL of a 10% solution) was added, the sample was mixed and the layers separated by centrifugation. The resulting fatty acid methyl esters extracted in the hexane layer were resolved by gas chromatography (GC). Hewlett Packard 5890GC (Wilmington, Del.) equipped with a SP2340 column (60 m, 0.25 mm ID, 0.20 micron film thickness) (Supelco, Bellefonte, Pa.). Column temperature was 150° C. at injection and the temperature programed from 150° C. to 200° C. at 2° C./min over 40 minutes. Injector and detector temperatures were 215° C. and 230° C., respectively.

Peroxide value, free fatty acids, and color: Peroxide values were determined by titration essentially by AOCS method Cd 8-53 and the data expressed as milliequivalents peroxide/kg oil. Free fatty acid values were determined by AOCS method Ca 5a-40 and the data expressed as % free fatty acids (as oleic acid). Color was measured using a Lovibond Tintometer and a 5¼" tube according to AOCS method Cc13b-45.

Tocopherol content: Tocopherol content was determined by normal phase HPLC using a Rainin Instrument Dynamax HPLC and data acquisition system equipped with a Milton Roy spectromonitor UV detector. HPLC conditions were: Waters µPorasil 3.9×300 mm silica column (unbonded, irregular shaped), a solvent system of hexane/isopropyl alcohol (98.5/1.5) with a flow rate of 1.5 mL/min Total run time for each sample was 7.0 minutes. Samples for HPLC analysis were prepared by adding 900 µL of hexane/isopropyl alcohol (98.5/1.5) to 100 µL of refined, bleached and deodorized oil. 40 µL was injected into the HPLC. Absorbance was monitored at 295 nm. Data are expressed as mg tocopherol/100 g of oil.

These data show the compositional analysis of the soybean oil of the invention and the vegetable oils with which it was compared. The performance of these oils was then further evaluated in the examples as discussed below.

TABLE 2

Composition and Chemical Analyses of Oils

| Oil Tested | Fatty Acid Composition | | | | | | PV | FFA | Color | | Additives | Tocopherol mg/100 G oil |
|---|---|---|---|---|---|---|---|---|---|---|---|---|
| | C16:0 | C18:0 | C18:1 cis | C18:1 trans | C18:2 | C18:3 | | | | | | |
| high oleic soybean | 6.4 | 3.3 | 85.6 | — | 1.6 | 2.2 | 0.01 | 0.01 | 0.5Y | 0.5R | — | 160.4 |
| normal soybean | 10.4 | 4.1 | 22.9 | — | 52.9 | 7.5 | 0.00 | 0.00 | 1.0Y | 0.2R | — | 160.9 |
| high oleic sunflower | 3.6 | 4.3 | 82.2 | — | 9.9 | 0.0 | 0.14 | 0.02 | 6.0Y | 0.4R | — | 46.0 |
| high oleic corn | 9.0 | 2.3 | 64.8 | — | 22.2 | 0.5 | 0.04 | 0.01 | 1.7Y | 0.3R | — | 72.8 |
| low linolenic soybean | 10.0 | 5.1 | 27.6 | — | 54.1 | 2.8 | 0.0 | 0.02 | 2.0Y | 0.4R | — | 89.3 |
| high oleic canola | 3.6 | 2.3 | 78.8 | — | 5.1 | 5.2 | 0.01 | 0.07 | 2.0Y | 0.3R | — | |
| soybean frying oil | 11.4 | 4.5 | 25.1 | — | 53.0 | 6.0 | 0.08 | 0.04 | 3.0Y | 0.5R | TBHQ, silicone | 112.8 |
| clear liquid shortening | 11.4 | 4.7 | 40.4 | 8.8 | 34.7 | 0.0 | 0.09 | 0.04 | 2.0Y | 0.3R | TBHQ, silicone | 112.2 |
| heavy duty shortening | 10.5 | 10.2 | 42.5 | 31.7 | 3.8 | 0.0 | 0.06 | 0.06 | 2.0Y | 0.4R | TBHQ, silicone | 110.0 |

Example 4

Oxidative Stability

The high oleic and normal soybean oils produced in Example 2 were evaluated for oxidative stability by AOM and OSI. All other commercial oils used for comparison were evaluated by OSI only. OSI determinations were made at 110° C. using the Oxidative Stability Instrument (Omnion, Inc, Rockland, Mass.) using official AOCS methods (AOCS Method Cd 12b-92). Samples were run in duplicate and the data presented are the average values for each sample. AOM determinations were made using official AOCS methods (Cd 12-57). The tests were run at 97.8° C. and the induction times given represent the number of hours required to reach 100 milliequivalents peroxide per kg of oil tested.

Figure 1:
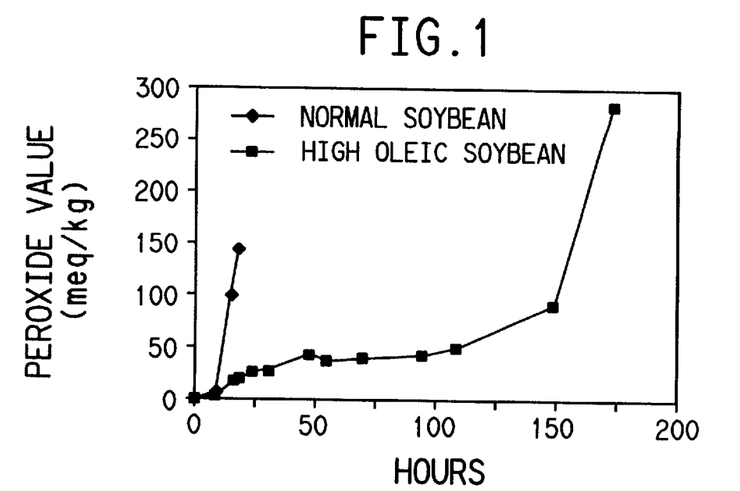
FIG. 1 depicts the peroxide values developed during the Active Oxygen Method test for high oleic soybean oil compared with normal soybean oil.

FIG. 1 shows a graph comparing the AOM results of high oleic and normal soybean oil. The average AOM induction time for high oleic soybean oil was 145 hours compared with 15 hours for normal soybean oil. The raw data used to make the graph is given in Table 3. Values obtained from the OSI determinations are given in Table 4. High oleic soybean oil had an OSI induction time of 80.7 hours compared with 6.9 hours for normal soybean oil.

TABLE 3

AOM values for normal and high oleic soybean oils

| Time (hours) | Normal Soybean Oil | High Oleic Soybean Oil |
|---|---|---|
| 0 | 0 | 0 |
| 7 | 9.77 | 1.93 |
| 15 | 97.06 | 11.68 |
| 17 | 141.04 | 15.2 |
| 23 | | 18.76 |
| 31 | | 20.83 |
| 46.5 | | 36.48 |
| 54.5 | | 31.1 |
| 70 | | 34.97 |
| 94 | | 41.75 |
| 108 | | 46.85 |
| 147.5 | | 86.84 |
| 171.5 | | 279.54 |

TABLE 4[a]

OSI induction times for various vegetable oils

| Oil | OSI Induction Time(hours) |
|---|---|
| high oleic soybean | 80.7 +/− 3.2 |
| normal soybean | 6.9 +/− 0.4 |
| high oleic sunflower | 18.2 +/− 0.1 |
| high oleic corn | 15.4 +/− 0.2 |
| low linolenic soybean | 6.5 +/− 0.3 |
| high oleic canola | 20.9 +/− 2.3 |
| soybean frying oil | 21.2 +/− 1.0 |
| clear liquid shortening | 31.8 +/− 0.9 |
| heavy duty shortening | 84.8 +/− 1.2 |

[a]The compositions of these oils are given in Table 2

Example 5

High Temperature Stability of High Oleic Soybean Oil

Figure 2A:
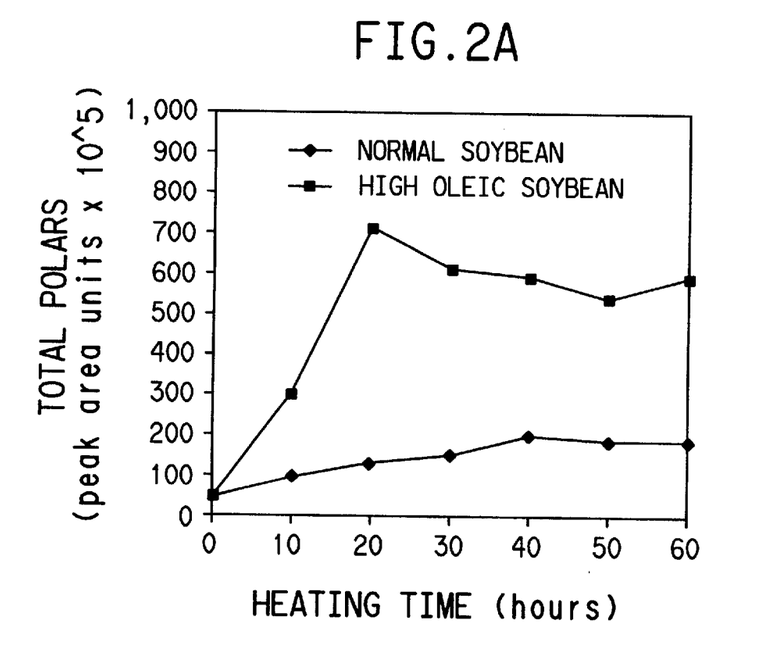
FIG. 2A presents the accumulation of polar materials in high oleic and normal soybean oils during heating of the oils.
Figure 2B:
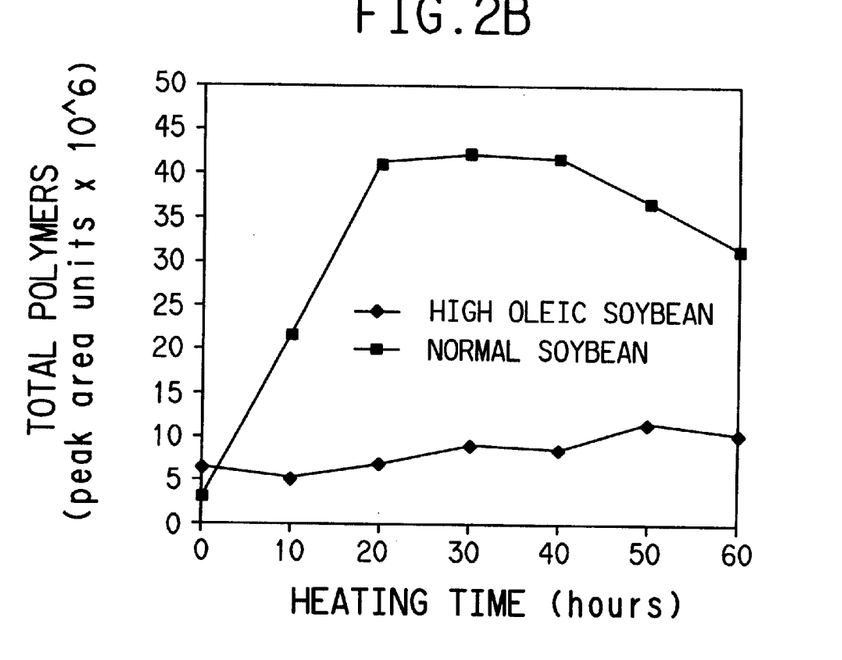
FIG. 2B presents the accumulation of polymeric materials in high oleic and normal soybean oils during heating of the oils.

High temperature stability of refined, bleached, and deodorized high oleic soybean oil produced in Example 2 was compared to the stability for normal soybean oil and other commercial oil samples. Stability was determined by heating the oils to frying temperature and monitoring the formation of polar and polymer degradation products by HPLC. High oleic soybean oil developed polar and polymer materials to a lesser extent than normal soybean oil as shown in FIG. 2A and 2B.

Sample Preparation: Oil samples (5 mL) were heated in glass tubes in an aluminum block on a hot plate controlled with a PMC Dataplate 520 temperature controller and timer. Oils were heated to 190° C. for 10 hours each day and allowed to cool before reheating. Fifty μL samples for HPLC analysis were collected after 10, 20, 30, 40, 50, and 60 hours of heating. Samples were stored at −20° C. until they could be assayed.

Reverse Phase High Performance Liquid Chromotogaphy: Methods used for reverse phase HPLC analysis of heated oils are similar to those of Lin (1991). Prior to HPLC analysis, 50 μL samples were brought to room temperature and 950 μL of an isopropyl alcohol /hexane (20:80, v/v) solution was added and the samples vortexed. The HPLC system consisted of a Rainin Instrument Dynamax HPLC and data acquisition system, two Rabbit-HP solvent delivery pumps, Spectra Physics SP8880/8875 Autosampler, and Milton Roy spectromonitor UV detector set at 254 μm. The column was a Beckman Ultrasphere 4.6×25 cm. Gradient conditions changed from 40:60 to 90:10 isopropanol:methanol over 37 minutes. Resulting chromatographs were integrated and the areas underneath the peaks corresponding to polar and polymeric materials identified. Data was expressed as total polar and total polymer peak area units.

Example 6

Schaal Oven Test

The oxidative stability of the instant high oleic soybean oil was also determined in an accelerated aging test known as a Schaal Oven Test. Oils used in this test were those produced in Example 2.

Figure 3:
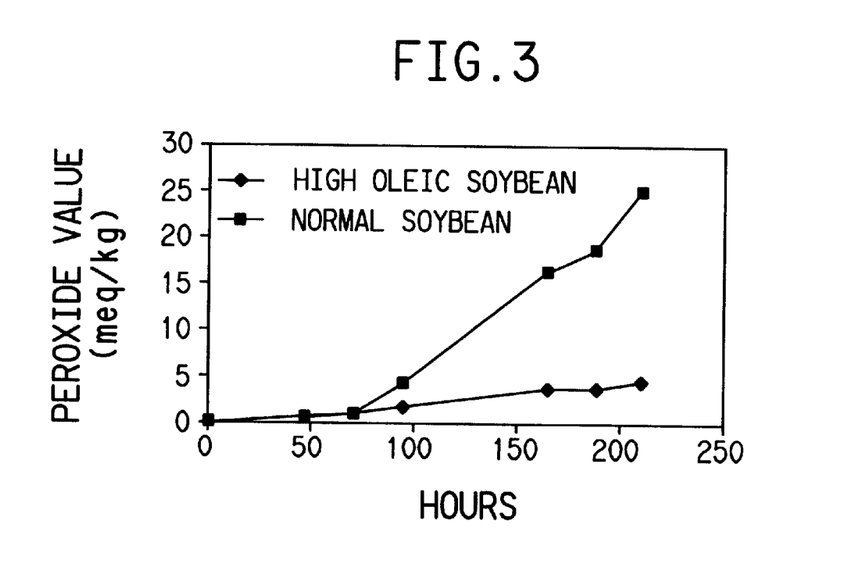
FIG. 3 compares the performance of high oleic soybean oil with normal soybean oil in the Schaal Oven test.

Oil samples (15 mL) were placed in a 30 mL beaker with a watch glass cover and kept in a forced draft oven at 63° C. Oxidative degradation was measured as titrable peroxide equivalents according to AOCS Method Cd 8-53. Samples for analysis were collected at various times during the heating of the oils. FIG. 3 presents the results from this test.

Example 7

The Effects of the Presence or Absence of Tocopherol on Oxidative Stability

Part A: Comparison of Normal and High Oleic Soybean Oils

Tocopherols are naturally occurring antioxidants and are present at different levels in different oilseeds. The tocopherol content of the extracted oils may also vary depending on the conditions used to manufacture the oil. Specifically, more or less tocopherol can remain in the oil depending on the time and temperature conditions used during deodorization. The tocopherol contents for high oleic and normal soybean oil were measured to determine if varying levels could be affecting stability of the two oils. These data are included in Table 2. High oleic and normal soybean oil did not differ in either total tocopherol content or in the ratio of individual tocopherols. While typical for the deodorizing conditions used here, these values are somewhat higher than values obtained for commercially produced oils which are generally around 100 mg total tocopherol/100 g oil, depending on the supplier. High oleic sunflower oil, high oleic corn oil and high oleic canola oil all had somewhat lower tocopherol contents than the soybean oils; these values ranged from 46 mg (sunflower) to 73 mg (corn) per 100 g oil.

High oleic soybean oil and the high oleic sunflower oil of Table 5 have similar fatty acid compositions with regard to oxidation potential. The difference between the OSI induction time for high oleic soybean (80.7) and high oleic sunflower (34.3 hours), suggests that factors other than fatty acid composition alone are affecting the oxidation rate. Tocopherols are known to exert a strong antioxidant affect which is dependent upon concentration. The soybean and sunflower oils differed in both the total tocopherol content and individual tocopherols present. To determine whether tocopherols were responsible for the difference in OSI, we added back individual tocopherols to achieve both the relative ratios and total amount of tocopherol (Table 4) present in the high oleic soybean oil. As shown in Table 5, the OSI of high oleic sunflower was increased to that of high oleic soybean by matching both the individual and total tocopherols present in high oleic soybean oil.

TABLE 5

The effect on OSI induction time of adding tocopherols to high oleic oils to match the content present in high oleic soybean oil

|  | High Oleic Soybean Oil | High Oleic Sunflower Oil |
|---|---|---|
| Fatty acid Composition | | |
| C16:0 | 6.4 | 3.0 |
| C18:0 | 3.3 | 4.3 |
| C18:1 | 85.6 | 87.0 |
| C18:2 | 1.6 | 4.1 |
| C18:3 | 2.2 | 0.0 |
| PV | 0.02 | 0.01 |
| FFA | 0.3 | 0.01 |
| total tocopherol (beginning) wt % (beginning) | 160.4 | 46.7 |
| alpha | 5.1 | 95.1 |
| gamma | 71.5 | 4.9 |
| delta | 23.4 | 0.0 |
| OSI (beginning) | 80.7 | 34.3 |
| total tocopherol (ending) wt % (beginning) | | 193.0 |
| alpha | | 25.1 |
| gamma | | 58.0 |
| delta | | 17.0 |
| OSI (ending) | | 74.6 |

The effect of tocopherols was also examined by producing high oleic soybean oils with lower tocopherol content (equal to concentrations found in high oleic sunflower) and measuring stability by AOM. The oils were produced by varying both the time and temperature during deodorization of refined, bleached high oleic soybean oil. Temperatures used were 240° C. and 265° C. Deodorization times ranged from 0 to 360 hours. Table 6 shows the deodorization conditions, the resulting oil compositions and AOM stability.

TABLE 6

Deodorization of High Oleic Soybean Oil

| Conditions | 1 | 2 | 3 | 4 | 5 | 6 | 7 |
|---|---|---|---|---|---|---|---|
| temperature, ° C. | 240 | 240 | 240 | 240 | 240 | 265 | 265 |
| time at temperature, min. | 0 | 30 | 60 | 120 | 240 | 240 | 360 |
| tocopherols, total, mg/100 g | 192.3 | 177.9 | 177.5 | 161.4 | 138.5 | 32.5 | 28.1 |
| AOM (hours) | 122.0 | 111.3 | 111.0 | 107.5 | 105.8 | 94.8 | 94.5 |

While tocopherol content was significantly reduced in the high oleic soybean oil, it can be seen from Table 6 that its oxidative stability, as measured by AOM induction time, was not reduced by more than 25% in the sample with the lowest tocopherol content. An induction time of 94 hours is significantly longer than the comparable OSI values for any of the other oils listed in Table 4.

Example 8

Hydrogenation of Normal and High Oleic Soybean Oils

This example illustrates the advantages of hydrogenating the high oleic soybean oil of this invention.

High oleic and normal soybean oils were hydrogenated using methods standard in the industry as described below.

Hydrogenation reactions were carried out using 0.04% nickel catalyst (Nysosel 325, Engelhard Corp), 75 ml oil, 104° C., under 90 psi hydrogen, stirred at 750 rpm in a reactor made by Autoclave Engineer, Inc., (EZE—Seal Reactor). Changes in the fatty acid composition of the oil during the reaction was monitored by refractive index. Oil samples were collected with iodine values (IVs) ranging from about 95 to 45. Oils were filtered through celite and deodorized using conditions described above. Hydrogenated oil samples were evaluated for free fatty acids, peroxides, fatty acid composition, and OSI induction time using the method described above. Solid fat index of each oil sample was determined using AOCS Method Cd 10-57. The solid fat index is a measure of the solids content at a given temperature, and is an important test in characterizing the physical properties of a fat.

TABLE 7

Properties of Hydrogenated High Oleic Soybean Oil

| Sample- IV | IV | Solid Fat Index | | | | | OSI (130° C.) | OSI (110° C.) | Calculated AOM (97.8° C.) | Trans Fatty Acids[a] | Time (minutes) |
| --- | --- | --- | --- | --- | --- | --- | --- | --- | --- | --- | --- |
| | | 50 (° F.) | 70 (° F.) | 80 (° F.) | 92 (° F.) | 104 (° F.) | | | | | |
| high oleic-78 | 78 | 6.2 | 4.9 | 5 | 4.6 | 4.3 | 33.8 | 134.6 | 325.6 | 3.7 | 19 |
| high oleic-71 | 71 | 13.1 | 8.2 | 8.1 | 7.6 | 6.2 | 52.6 | 209.9 | 508.0 | 7.3 | 30 |
| high oleic-59 | 59 | 32 | 23.8 | 21.3 | 18.6 | 13.7 | 64.4 | 256.9 | 622.0 | 12.4 | 45 |
| high oleic-46 | 46 | 57.3 | 50.7 | 49.5 | 46 | 36.6 | 95.1 | 379.1 | 918.0 | 17.2 | 65 |
| normal soybean | 95 | 9.3 | 6 | 6 | 4.4 | 2.9 | 5.1 | 20.4 | 49.0 | 11.9 | 45 |
| normal soybean | 92 | 11.9 | 8.1 | 7.3 | 5.3 | 3.2 | 4.8 | 18.9 | 45.4 | 14.8 | 55 |
| normal soybean | 83 | 14.4 | 8.6 | 8.2 | 5.5 | 3.2 | 9.1 | 36.3 | 87.3 | 14.2 | 130 |
| normal soybean | 72 | 27.6 | 17.5 | 16.5 | 10.1 | 6 | 19.2 | 76.7 | 185.3 | 17.0 | 145 |
| normal soybean | 63 | 50 | 40.3 | 38.7 | 28.3 | 18 | 47.2 | 188.3 | 455.7 | 17.8 | 185 |
| normal soybean | 49 | 59.6 | 52.9 | 51.2 | 41 | 29.6 | 63.4 | 252.9 | 612.3 | 17.5 | 245 |

[a]As a percentage of total fatty acids

Figure 4:
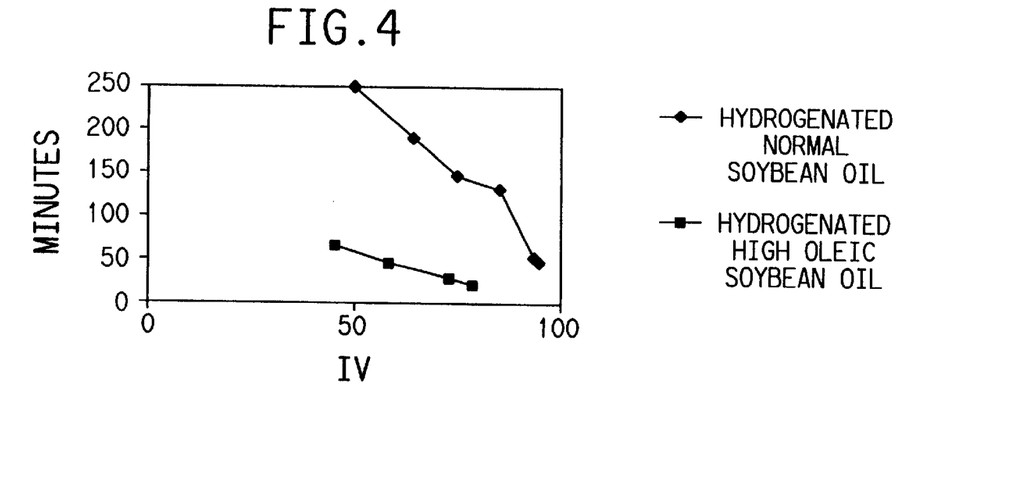
FIG. 4 compares the times required to make equivalent products as indicated by iodine value (IV) from hydrogenation of high oleic and normal soybean oils.
Figure 5:
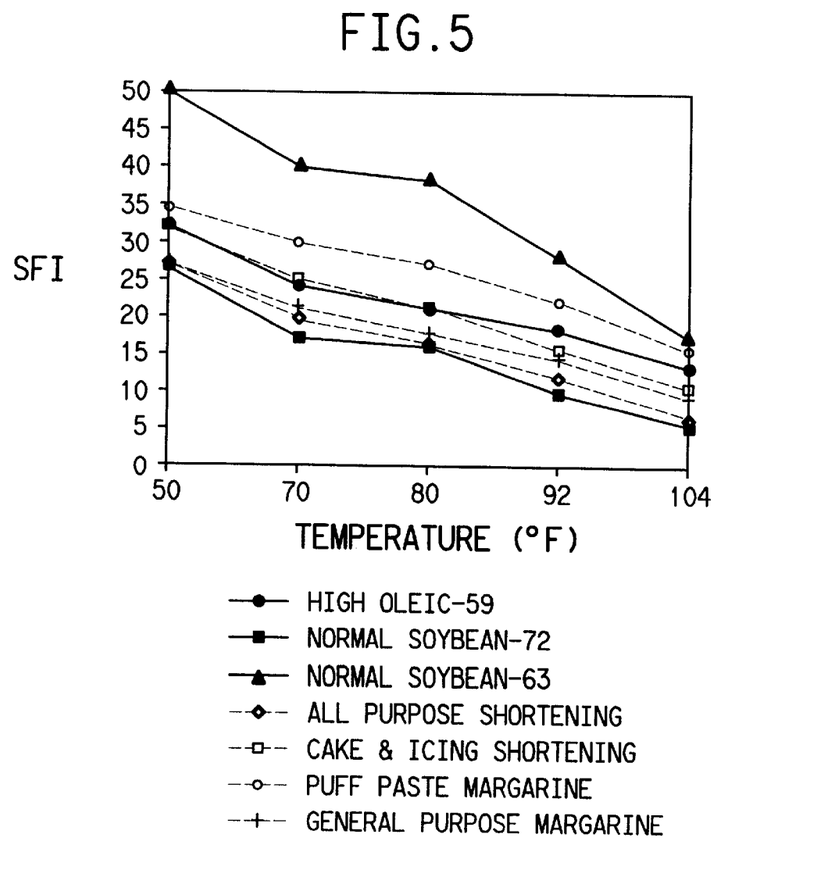
FIG. 5 presents the Solid Fat Index measurements of a hydrogenated high oleic soybean oil compared with other fats.

Using high oleic soybean oil as the base oil for hydrogenation reactions has several advantages over using normal soybean oil. Significantly less time is required to reach any given product, as represented by IV, from high oleic soybean oil when compared with normal soybean oil (FIG. 4). The resulting hydrogenated products also have several advantages including lower trans fatty acids and substantially longer OSI induction times. FIG. 5 presents the solid fat index values for one of the hydrogenated high oleic soybean oil products compared with hydrogenated normal soybean oil products and a variety of commercial fats.

Example 9

Stability of high oleic soybean oil as a function of composition

Oil from high oleic soybean seed grown during subsequent growing seasons was harvested and the oil extracted and processed by the conditions set forth in Example 2. Compositional data was obtained using the methods described in Example 3. High oleic soybean oils from these productions varied slightly in fatty acid composition, tocopherol content, and AOM/OSI induction times as shown in Table 8.

TABLE 8

Composition and stabilities of soybean oils

| | IA, 95 | PR, 95 | IA, 96 | (Control) |
| --- | --- | --- | --- | --- |
| Fatty Acid Composition | | | | |
| C16:0 | 6.3 | 7.1 | 6.4 | 10.1 |
| C18:0 | 3.7 | 3.7 | 3.1 | 3.5 |
| C18:1 | 84.0 | 81.7 | 82.6 | 17.9 |
| C18:2 | 1.6 | 2.0 | 2.3 | 58.6 |
| C18:3 | 2.4 | 3.6 | 3.7 | 8.2 |
| Quality | | | | |
| PV | 0.0 | 0.0 | 0.06 | |
| FFA | 0.01 | 0.01 | 0.01 | |
| color | 1.5Y | 0.9Y | 1.8Y | |
| | 0.3R | 0.1R | 0.2R | |
| AOM, hr | 141 | 107 | 82 | 14 |
| OSI, hr | 52–80 | 56–63 | 43 | 6 |
| tocopherols (mg/100 g) | 137 | 170 | 87.9 | |
| gamma | 101.0 | 115.0 | 54.9 | |
| delta | 25.5 | 43.5 | 29.6 | |
| alpha | 10.1 | 11.0 | 3.4 | |

Example 10

High oleic soybean oil as a blending source

Part A: Blending with normal soybean oil

High oleic soybean oil produced in Example 2 was blended with normal soybean oil to varying percentages and the oxidative stability of the blended oils was evaluated by OSI. Table 9 shows the effect the increase in oxidative stability of normal soybean oil by blending with high oleic soybean oil.

TABLE 9

The effect on oxidative stability of normal soybean oil by blending with high oleic soybean oil.

| % normal soybean oil | OSI | Fatty Acid Composition |
| --- | --- | --- |

| in blend | (hrs) | C16:0 | C18:0 | C18:1 | C18:2 | C18:3 |
|---|---|---|---|---|---|---|
| 0 | 76.4 | 6.3 | 3.7 | 84.6 | 1.7 | 2.3 |
| 2.5 | 63.9 | 6.6 | 3.6 | 82.9 | 3 | 2.5 |
| 5 | 46.3 | 6.7 | 3.4 | 80.9 | 4.6 | 2.6 |
| 10 | 38.4 | 6.9 | 3.7 | 78.4 | 6.9 | 2.8 |
| 15 | 30.5 | 7 | 3.7 | 75.8 | 9.1 | 3.1 |
| 20 | 25.7 | 7.4 | 3.8 | 72.9 | 11.5 | 3.3 |
| 100 | 6.0 | 10.1 | 3.5 | 17.9 | 58.6 | 8.2 |

Part B: Blending with low linolenic acid soybean oil

High oleic soybean oil produced in Example 2 was blended with a low linolenic acid soybean oil and the resulting blend evaluated for oxidative stability by OSI. Table 10 shows the composition and oxidative stability of the blend.

TABLE 10

The effect on oxidative stability of low linolenic soybean oil by blending with high oleic soybean oil

| % low linolenic soybean oil in blend | C16:0 | C18:0 | C18:1 | C18:2 | C18:3 | OSI Induction Time (hours) |
|---|---|---|---|---|---|---|
| 0 | 6.4 | 3.7 | 84.4 | 1.0 | 2.2 | 72.7 |
| 50 | 7.3 | 4.0 | 61.2 | 23.2 | 2.6 | 18.6 |
| 100 | 8.3 | 4.3 | 37.7 | 44.4 | 3.4 | 10.9 |

Example 11

Evaluation of high oleic soybean oil use in industrial fluid and hydraulic fluid applications The performance of the oil of this invention use in industrial fluid and hydraulic fluid applications was compared to commercially available industrial oil products using the rotary bomb oxidation test (RBOT) (ASTM D-2272). This test is used to evaluate the oxidation characteristics of turbine, hydraulic, transformer and gear oils. The test apparatus consists of a pressurized bomb axially rotating at an angle of 300 from the horizontal in a bath at 150° C. Fifty grams of test oil with or without commercial additive and 5 g of water are charged to the bomb containing a copper catalyst coil. The bomb is initially pressurized with oxygen to 90 psi at room temperature. The 150° C. bath temperature causes this pressure to increase to approximately 200 psi. As oxidation occurs, the pressure drops, and the failure point is taken as a 25 psi drop from the maximum pressure attained at 150° C. The results are reported as the number of minutes to the 25 psi loss, as shown in Table 11 below.

TABLE 11

Performance of oils in Rotary Bomb Oxidation test

| Oil | RBOT Minutes |
|---|---|
| high oleic soybean oil, no additive | 22 |
| high oleic soybean oil + 4.5% Lubrizol 7653 | 250 |
| control soybean oil, no additive | 18 |
| control soybean oil + 4.5% Lubrizol 7653 | 49 |
| Mobil EAL 224H (canola-based) hydraulic fluid | 29 |
| Mobile DTE 13M (petroleum-based) | 216 |
| Pep Boys ATF (petroleum-based) | 135 |

These data show the superior performance of the oil of the present invention in industrial fluid and hydraulic fluid applications which require high oxidative stability.

What is claimed is:

1. A high oleic soybean oil having high oxidative stability which comprises a C18:1 content of greater than 75% of the fatty acid moieties in the oil, a combined C18:2 and C18:3 content of less than 10% of the fatty acid moieties in the oil, and an active oxygen method induction time of greater than 50 hours wherein said oxidative stability is achieved without the addition of an antioxidant.

2. The high oleic soybean oil having high oxidative stability according to claim 1 wherein said oil is useful as a blending source to make a blended oil product.

3. The high oleic soybean oil having high oxidative stability according to claim 1 wherein said oil is useful in the preparation of food.

4. The high oleic soybean oil having high oxidative stability according to claim 1 wherein said oil is further processed, said processing being selected from the group consisting of hydrogenation, fractionation, interesterification, and hydrolysis.

5. A food which has improved stability against oxidation by having incorporated therein the oil of claim 1.

6. Products made from the hydrogenation, fractionation, interesterification or hydrolysis of the oil of claim 1.

7. A blended oil product made with the oil of claim 1.

8. By-products made during the production of the oil of claim 1.

* * * * *